United States Patent [19]

Proctor

[11] 3,972,321

[45] Aug. 3, 1976

[54] UPPER LIP MOUNTED RETAINING MEANS FOR MEDICAL-SURGICAL TUBES

[76] Inventor: John S. Proctor, 11924 Beltsville Drive, Apt. No. 33, Beltsville, Md. 20705

[22] Filed: Feb. 20, 1975

[21] Appl. No.: 551,262

[52] U.S. Cl. .......................... 128/348; 128/DIG. 26; 128/206; 128/208
[51] Int. Cl.² ........................................ A61M 25/02
[58] Field of Search ................ 128/348, 349, 350 R, 128/351, 205–209, 146.7, DIG. 26, 133

[56] References Cited
UNITED STATES PATENTS

| | | | |
|---|---|---|---|
| 2,670,735 | 3/1954 | Brody | 128/133 |
| 2,735,432 | 2/1956 | Hudson | 128/206 X |
| 3,082,767 | 3/1963 | Matheson | 128/146.7 |
| 3,161,199 | 12/1964 | Sands | 128/348 |
| 3,288,137 | 11/1966 | Lund | 128/133 |
| 3,702,612 | 11/1972 | Schlesinger | 128/350 R |
| 3,730,187 | 5/1973 | Reynolds | 128/DIG. 26 |
| 3,782,388 | 1/1974 | Page | 128/348 |
| 3,924,636 | 12/1975 | Addison | 128/351 |

Primary Examiner—Dalton L. Truluck
Attorney, Agent, or Firm—Laurence R. Brown

[57] ABSTRACT

A non-adhesive retaining device for medical-surgical tubes, such as endotracheal tubes or nasal cannulae, have a soft plastic staging member held by a headband in contact with the upper lip adjacent to the nose with a latex rubber cuff band grasping the tube. This assembly forms a sanitary type simple mount that engages the skin to hold the tube in place at the facial entrance. The cuff grasps the tube to secure it without lateral, rotational or axial movement. This retaining device serves as a comfortable flexible means that will conform to normal body movement and handling without irritation to skin or facial entrance. The staging member when contacting the lip area has at the center a protruding arm extending at an angle to retain at its center end the cuff that surrounds the tube in position for entry straight into the facial passage without bending or rubbing on the rim of the patients nostril or mouth as the case may be. The member is reversible to extend the tubing at a convenient angle into either the nostril or mouth.

2 Claims, 5 Drawing Figures

UPPER LIP MOUNTED RETAINING MEANS FOR MEDICAL-SURGICAL TUBES

This invention relates to improvements in medical-surgical tube retainers, and in particular it relates to headband mounted nasal or endotracheal tube retainers for holding the tubes in position to enter a facial opening of a patient during surgery or medical treatment.

BACKGROUND

Nasal cannula are conventionally held in place by adhesive tape placed across the nose, forehead or cheek of the patient.

These areas are characteristically oily, thus greatly reducing the holding power of the adhesive.

The procedures for which these tubes are used generally involve either the introduction (gavage) or evacuation (lavage) of fluids to/from the patient's stomach. The presence of any of this fluid on the tape or surrounding skin areas will cause a loosening effect upon the adhesive.

The tubes are usually placed in patients that are critically ill, and which exhibit various symptoms of shock. One of the most common of which manifests itself as facial perspiration, thereby greatly impairing the adhesive characteristics of the tape.

The skin of the face is quite sensitive, and a number of people exhibit immediate allergic reactions to adhesive tape. Many other people develop a sensitivity after varying periods of time. This secondary reaction is often seen as reddening and blistering of the skin beneath and around the taped area. These reactions are present in both the male and female, and depend to a great degree upon the individual. In both critical-intensive and extended care situations (where long term usage of such tubes is common), this sensitivity could easily result in rapid tissue breakdown, sloughing, and the onset of infection. Infection, however slight, in these situations could prove extremely dangerous. This would also provide no sound alternative for retaining the tube once this situation had arisen.

Endotracheal tubes are used during major surgical procedures to insure a maximum airway is available and to provide proper ventilation of the patient under general anesthesia.

They are also used to provide an artificial airway in emergency situations where the larnyx is swollen or spasm restricted, or the patient is unconscious and an airway is deemed necessary in the event that immediate resucitation is needed.

They are also used in patients where an airway is continually maintained, such as intensive care units or extensive care facilities.

Adhesive tape, secured across the patient's cheek, is commonly used as a secondary means to hold endotracheal tubes in place. Their primary means is an inflatable cuff at the distal (larnyx) end that when inflated presses against the walls of the larynx holding it in place. However, improper inflation, leakage, or accidental deflation of this cuff immediately transfers the security (life-supporting) retention of this tube to the adhesive tape — therefore, it is of vital concern.

Since the endotracheal tube is introduced into the larnyx by means of the mouth, there is always some moisture involved. It is not uncommon at all for the adhesive tape to come loose in even the most controlled of situations.

The retention of this tube is obviously a critical factor. The loss of the airway it provides has proven fatal — since reinsertion of the tube can often be difficult if not impossible because of a swollen or spasmed larnyx. And an emergency tracheotomy consumes critical minutes that the brain goes without oxygen.

The aforementioned allergic reactions to this adhesive tape method also apply here. Perhaps to an even greater degree, since larger strips of tape are commonly needed to hold this larger tube.

Another problem would be that taping a tube in this area is extremely difficult, if not impossible, in bearded individuals.

Prior art headband mounted cannula holders are known as represented for example by U.S. Pat. Nos. 2,735,432; 2,931,358; 3,161,199; and 3,648,703. However, these prior art type of holders have presented various problems such as the following:

They necessitate auxiliary adhesive tape mounts.

They are not elastic to permit movement and comfort while holding the cannula firmly in proper position.

The tubes are bent or held so they may become fouled or pinched.

They are not held in the proper place for comfort and avoidance of skin or tissue irritation.

They do not firmly grasp the cannula to prevent axial or lateral movement.

They do not hold the cannula in place to observe the contents.

They provide constructional features which will accumulate mucus, secretions or bacteria in an unsanitary manner.

OBJECTIVES OF THE INVENTION

It is a general object of this invention to provide improved medical-surgical tubing retainers for holding them on a patient during use that will correct one or more of the foregoing deficiencies.

It is a more specific object of this invention to provide a sanitary and inexpensive retainer for surgical tubes.

Another object of the invention is to provide a headband type tube retainer that will stay in place and position the tubing comfortably while in use in the mouth or a nostril.

Further objects, features and advantages will be made evident throughout the following specification.

BRIEF DESCRIPTION

In accordance with this invention, a single strip of latex rubber or other similar soft plastic resilient materials is formed into a cylindrical cuff retainer for holding a nasal cannula or endotracheal tube while in use in a patient. The strip is held on the extremity of a centrally located arm disposed on a plastic staging member having a panel strip engaging the patient's upper lip to thereby be flexible enough to conform with normal body movement. The staging member is elastically held in contact with the upper lip of the patient by a headband which is bifurcated to extend around the patient's ears, to form a simple sanitary assembly adaptable to various tubing sizes.

THE DRAWINGS

In the drawings is shown a preferred embodiment of the invention, wherein.

DETAILED DESCRIPTION

Figure 3:
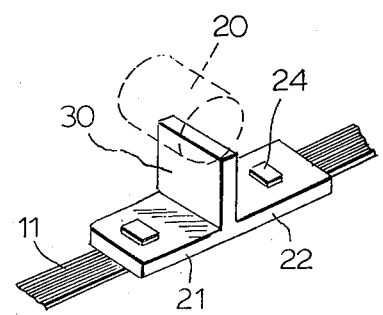
FIG. 3 is a perspective top view of a preferred staging member embodiment afforded by this invention.

Now with reference to the drawings, like reference characters represent similar features throughout the various views. As may be seen in FIG. 1, a surgical patient 10 has a headband assembly 11 with two bifurcated bands 12, 13 extending on either side of ear 14 to hold the tube retainer assembly 17 in place upon the upper lip 16 in a manner shown in more detail in FIGS. 2 and 3. The mount assembly 17 in this view holds in place in a nostril the cannula 18.

A cylindrical cuff 20 for grasping the cannula is made of a soft latex rubber strip which is held on the extremity of an arm 30 perpendicular to two diametrically opposed extending end portions 21, 22 of a staging member panel which will lie flat upon the patient's upper lip 16 as held in place by headband 11. The latex material may be obtained commercially for example from Perry Rubber Co., and also may be an equivalent soft elastic plastic of similar properties. The staging member can be fashioned from a vinyl plastic panel, or the like, about 1 centimeter wide, 1 millimeter thick and about 5 centimeters long.

When in place the staging member ends 21 and 22 and extending arm 30 are elastic enough to provide conformation to a normal range of body movement. The grasping properties of the latex cuff serve to hold tube 18 in place in a nostril without lateral, rotational or axial slippage and the entire assembly provides a sanitary device that does not tend to inflame the skin or catch mucus and bacteria. The headband 11 is connected frictionally through a slit in the flat semi-rigid soft plastic staging panel 23 by means of stopper head tab member 24. Thus, the headband may be adjusted for proper size and elastic tension by pulling on metal tab 24 to pull the band through the aperture in the end panel 21 or 22.

Figure 4:
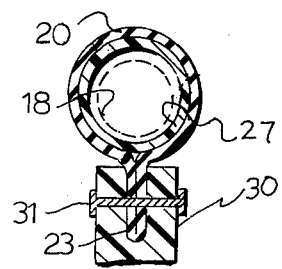
FIG. 4 is an end elevation view partly broken away, in detail section, of the mouth assembly having a cylindrical shipping form for slipping along a tube to facilitate shipping and placement of the retainer assembly.

As seen in FIG. 4, the latex staging member cuff cylinder 20 is held at the extremity of the normally extending staging member arm 30, which can be of variable length to position the encompassed tube away from the lip far enough to enter the nostril naturally without bending, discomfort, pressure or inflammation. The latex strip 20 may be secured in a slot 23 by having two ends frictionally squeezed and held by rivet member 31.

The cuff portion 20 is expandable to fit variable size tubes and provides an elastic-frictional grasp that prevents rotary or axial movement of the tube 18, yet flexible enough to adjust to normal movements of the patient or directions of the tubing orientation that may occur with nostrils or different shape, etc. Also the latex cuff 20 mounting feature permits axial adjustment of the tube 18 and will mount at any desired position along its length.

Figure 1:
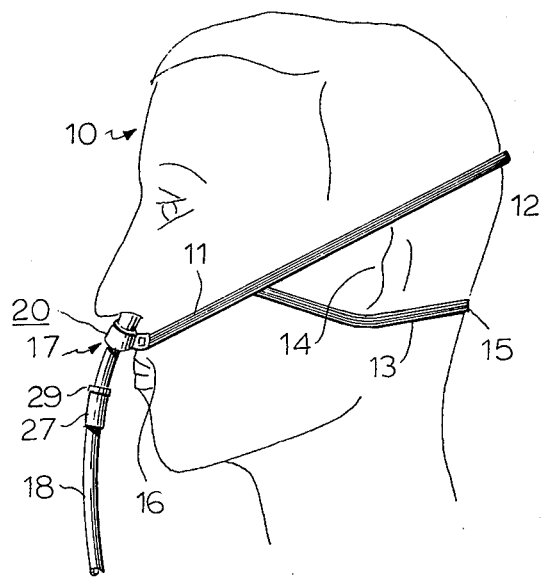
FIG. 1 is a profile view of a patient having a nasal cannula held in place by a headband retainer assembly afforded by this invention.
Figure 2:
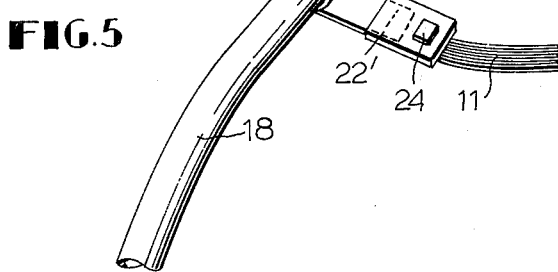
FIG. 2 is a detailed profile view of the retainer assembly holding an endotracheal tube in place in a patient's mouth.

To facilitate the location of cuff 20 along tube 18, a cylindrical sleeve 27 may be used as an internal cuff retainer having a dimension to just fit over tube 18 and slide therealong. The cuff 20 is then manufactured and shipped in place on the sleeve 27, as indicated by the phantom view of the tube 18 in FIG. 4. Thus, when placed in the axial tube location desired, the sleeve 27 may be slipped out and retained about tube 18 as shown in FIGS. 1 and 2 for future use in the event a readjustment or removal is desirable. The cuff is easily manually manipulated but it may be desirable to have retaining lip 29 placed on the distal end of the sleeve for manual aid in grasping it and removing it from the rubber cuff at the desired mount position on the tubing 18.

As may be seen from FIG. 2, the staging member arm 30 is preferably extended at some angle 35 of about 70° from the staging member panel. This provides the advantage of holding tube 18 for proper entry into the mouth as shown for endotracheal tube usage. Furthermore, when the nasal passage is used the panel is simply reversed and the angle is proper for entering a nostril without friction or rubbing on the rim, thereby reducing irritation and discomfort presented by taping tubes in place.

Figure 5:
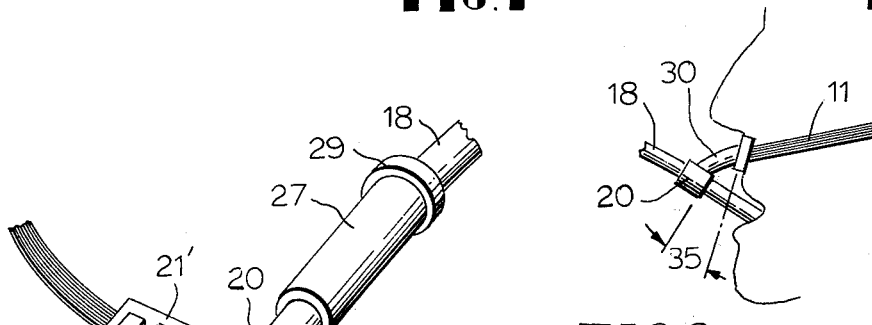
FIG. 5 is a perspective detail view of the construction of an alternative retainer assembly for holding a tube as provided by this invention.

An alternative simplified view as shown in FIG. 5 might be used in some cases, where the latex strip forming the cuff has ends extended to meet the staging member platform ends 21' and 22'. This view shows the holder cylinder 27 in place about the tube 18 when the cuff 20 is positioned along its length.

As may be appreciated from the foregoing description the cuff 20 mounting technique and the assembly provided by the invention has several distinct advantages over prior art surgical tube retainers, including the following:

a. The encircling cuff grasps and holds the tube in place.
b. The thin natural latex rubber provides a high coefficient of friction between the cuff and tube so that it impedes accidental slipping, rotating or dislodging.
c. The cuffs can expand to accommodate various sizes or can be manufactured for different size ranges of standard surgical tubes. Normal non-expanded cuff dimensions are about 75% of the circumference of the tube to be held.
d. The cuff will accommodate either nasal cannula or endotracheal tubes that enter the mouth merely by changing axial direction of the working end.
e. The cuff can be packed for shipping upon the sleeve member 27 which permits easy mounting or repositioning. This sleeve can be a rigid plastic sleeve of about 2 centimeters thickness.
f. The arm 30 region provides a mounting angle into the nostril so that skin friction and irritation may be eliminated.
g. Sanitary conditions can be maintained without a tendency to accumulate body secretions or bacteria.
h. The mount stays in place in presence of perspiration or dampness and when a patient moves about.

Having therefore set out various features and advantages in the improved mounting means for surgical tubes, those novel features believed descriptive of the spirit and scope of the invention are set out with particularity in the appended claims.

What is claimed is:

1. Improved retaining means for holding a medical-surgical tube in position on a patient while in use comprising in combination, a soft flexible elastic strip forming a cylindrical cuff for receiving said tube in place thereinside having a staging mount for holding the cuff affixed thereto in position extending from an upper lip of the patient, and a headband affixed to said staging mount to elastically retain it in place on said upper lip wherein a cylindrical sleeve member is provided of a diameter such that it slides concentrically along said tube, and said cuff is elastically expanded and positioned on the outer circumference of said sleeve member for transport and positioning.

2. Improved retaining means for holding a medical-surgical tube in position on a patient while in use comprising in combination, a soft flexible elastic strip forming a cylindrical cuff for receiving said tube in place thereinside having a staging mount for holding the cuff affixed thereto in position extending from an upper lip of the patient, and a headband affixed to said staging mount to elastically retain it in place on said upper lip having a substantially rigid arm extending between said cuff and said staging mount in a plane substantially normal to said upper lip to space said cuff away from the patient's upper lip when in place to enter the tube into a facial opening wherein said normally extending arm extends from said staging mount in said plane at an angle of the order of 70° for resting on the upper lip with said arm extending downwardly to expedite entry of the tube into the oral facial opening and with said mount reversed with said arm extending upwardly to expedite entry of the tube into the nasal facial opening.

* * * * *